(12) United States Patent
Clague et al.

(10) Patent No.: US 7,081,227 B2
(45) Date of Patent: Jul. 25, 2006

(54) AMPHIPHILIC MEDIATED SAMPLE PREPARATION FOR MICRO-FLOW CYTOMETRY

(75) Inventors: David S. Clague, Livermore, CA (US); Elizabeth K. Wheeler, Livermore, CA (US); Abraham P. Lee, Irvine, CA (US)

(73) Assignee: The Reagents of the University of California, Oakland, CA (US)

( * ) Notice: Subject to any disclaimer, the term of this patent is extended or adjusted under 35 U.S.C. 154(b) by 0 days.

(21) Appl. No.: 10/862,998

(22) Filed: Jun. 7, 2004

(65) Prior Publication Data
US 2005/0272096 A1 Dec. 8, 2005

(51) Int. Cl.
*G01N 21/00* (2006.01)

(52) U.S. Cl. .............................. 422/81; 422/82; 422/50; 422/68.1; 436/518; 436/524; 436/52; 435/7.1; 435/287.1

(58) Field of Classification Search .................. 422/50, 422/55, 68.1, 82.05, 81, 82; 435/4, 7.1, 283.1, 435/287.1, 287.2, 288.1, 288.7, 288.4; 436/52, 436/501, 518, 524, 532, 528
See application file for complete search history.

(56) References Cited

U.S. PATENT DOCUMENTS

| | | | |
|---|---|---|---|
| 4,735,504 A * | 4/1988 | Tycko | 356/336 |
| 5,055,390 A | 10/1991 | Weaver et al. | |
| 5,364,531 A | 11/1994 | Bignami et al. | |
| 5,726,404 A | 3/1998 | Brody | |
| 5,744,709 A | 4/1998 | Saripalli et al. | |
| 6,074,879 A * | 6/2000 | Zelmanovic et al. | 436/10 |
| 6,297,061 B1 * | 10/2001 | Wu et al. | 436/518 |
| 6,454,945 B1 | 9/2002 | Weigl et al. | |
| 6,656,470 B1 * | 12/2003 | Bowersock et al. | 424/184.1 |
| 6,808,882 B1 * | 10/2004 | Griffiths et al. | 435/6 |
| 2003/0003476 A1 * | 1/2003 | Kinoshita et al. | 435/6 |
| 2003/0209059 A1 * | 11/2003 | Kawano et al. | 73/53.01 |
| 2004/0029978 A1 * | 2/2004 | Chane-Ching | 516/9 |
| 2004/0202682 A1 * | 10/2004 | Emrick et al. | 424/400 |
| 2004/0234588 A1 * | 11/2004 | Lu Et al. | 424/450 |

* cited by examiner

Primary Examiner—Long V. Le
Assistant Examiner—Melanie J. Yu
(74) Attorney, Agent, or Firm—Eddie E. Scott; Alan H. Thompson

(57) ABSTRACT

A flow cytometer includes a flow cell for detecting the sample, an oil phase in the flow cell, a water phase in the flow cell, an oil-water interface between the oil phase and the water phase, a detector for detecting the sample at the oil-water interface, and a hydrophobic unit operatively connected to the sample. The hydrophobic unit is attached to the sample. The sample and the hydrophobic unit are placed in an oil and water combination. The sample is detected at the interface between the oil phase and the water phase.

12 Claims, 3 Drawing Sheets

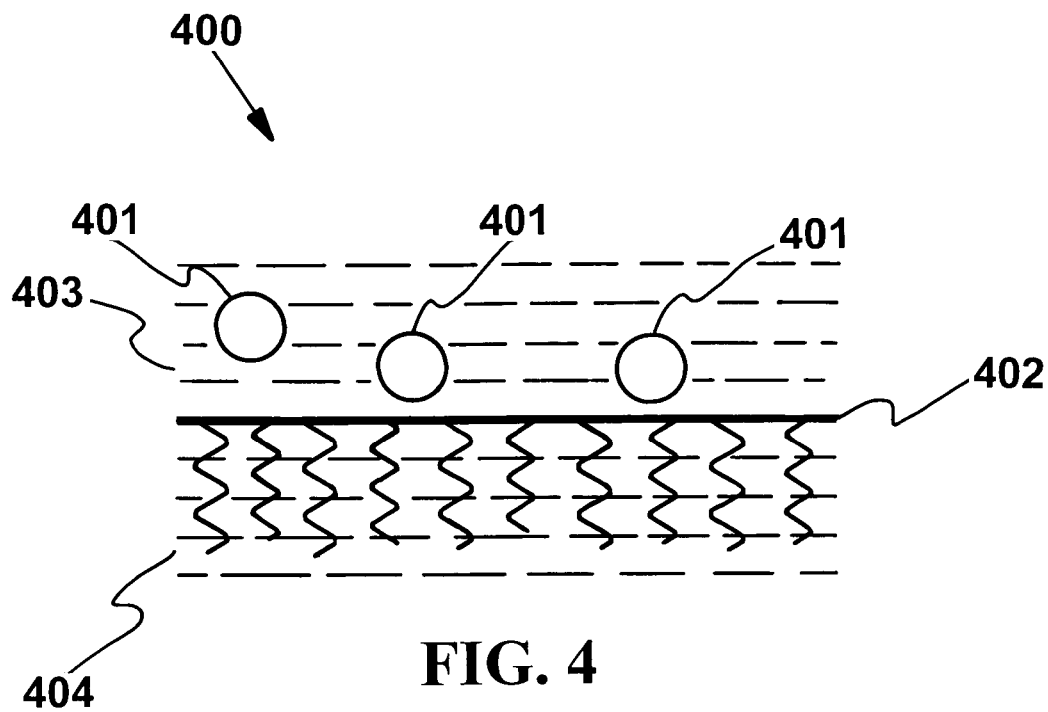
FIG. 4
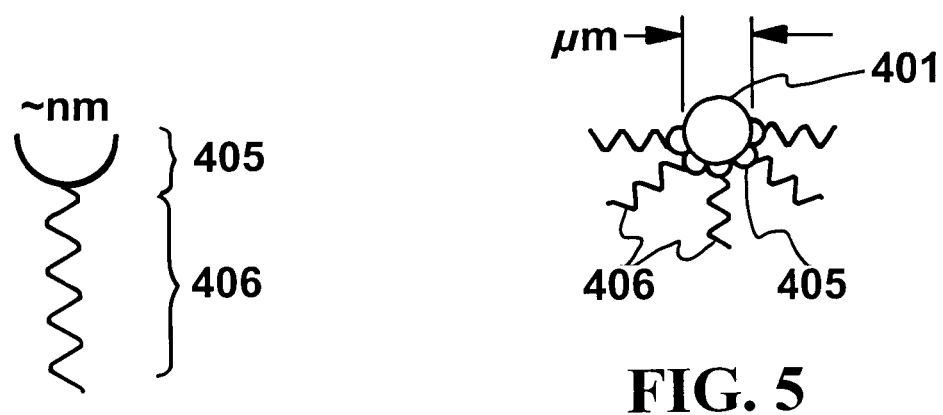
FIG. 6
FIG. 5

AMPHIPHILIC MEDIATED SAMPLE PREPARATION FOR MICRO-FLOW CYTOMETRY

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to micro-flow cytometry and more particularly to amphiphilic mediated sample preparation for micro-flow cytometry.

2. State of Technology

U.S. Pat. No. 5,726,404 issued Mar. 10, 1998 to James P. Brody for a valveless liquid microswitch provides the following state of technology information, "Integrated microfluid handling systems that provide control over nanoliter sized volumes of liquid will be extraordinarily useful in both miniaturizing present analytical tests and handling the small sample sizes frequently used in biomedical testing. The goal is to perform the entire chemical analysis in a single micromachined device, from preliminary treatment of the sample, to mixing of reagents, separation of the analyte of interest, measurement of the analyte, and further mixing, separation and measurement stages. Among the micromachined components required are channels, valves, pumps, flow sensors, mixing chambers and optical detectors."

U.S. Pat. No. 6,454,945 issued Sep. 24, 2002 to Bernhard H. Weigl et al. for microfabricated devices and methods provides the following state of technology information, "microfabricated systems for extraction of desired particles from a sample stream containing desired and undesired particles. The sample stream is placed in laminar flow contact with an extraction stream under conditions in which inertial effects are negligible. The contact between the two streams is maintained for a sufficient period of time to allow differential transport of the desired particles from the sample stream into the extraction stream. In a preferred embodiment the differential transport mechanism is diffusion. The extraction system of this invention coupled to a microfabricated diffusion-based mixing device and/or sensing means allows picoliter quantities of fluid to be processed or analyzed on devices no larger than silicon wafers. Such diffusion-based mixing or sensing devices are preferably channel cell systems for detecting the presence and/or measuring the quantity of analyte particles in a sample stream."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a flow cytometry system for detecting a sample comprising attaching a hydrophobic unit to the sample, providing an oil and water combination with an interface between the oil and the water, placing the sample and the hydrophobic unit in the oil and water combination allowing the sample and the hydrophobic unit to reach the interface, and detecting the sample at the interface. The flow cytometry system of the present invention includes a flow cell, an oil component in the flow cell, a water component in the flow cell, an oil-water interface between the oil component and the water component, a detector that detects the sample at the oil-water interface, and a hydrophobic unit operatively connected to the sample.

The flow cytometry system of the present invention has use for quantitative cell, bead and other particle differentiation. Today's commercially-available systems are relied upon for an array of applications including monitoring in cancer and HIV infection. Furthermore, the present invention presents a viable scheme to miniaturize this important technology, which will significantly increase its impact.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 4 is an illustration of another embodiment of a system constructed in accordance with the present invention.

FIG. 5 is an illustration of some of the components of the system illustrated in FIG. 4.

FIG. 6 is an illustration of some of the components of the system illustrated in FIG. 5.

DETAILED DESCRIPTION OF THE INVENTION

Figure 1:
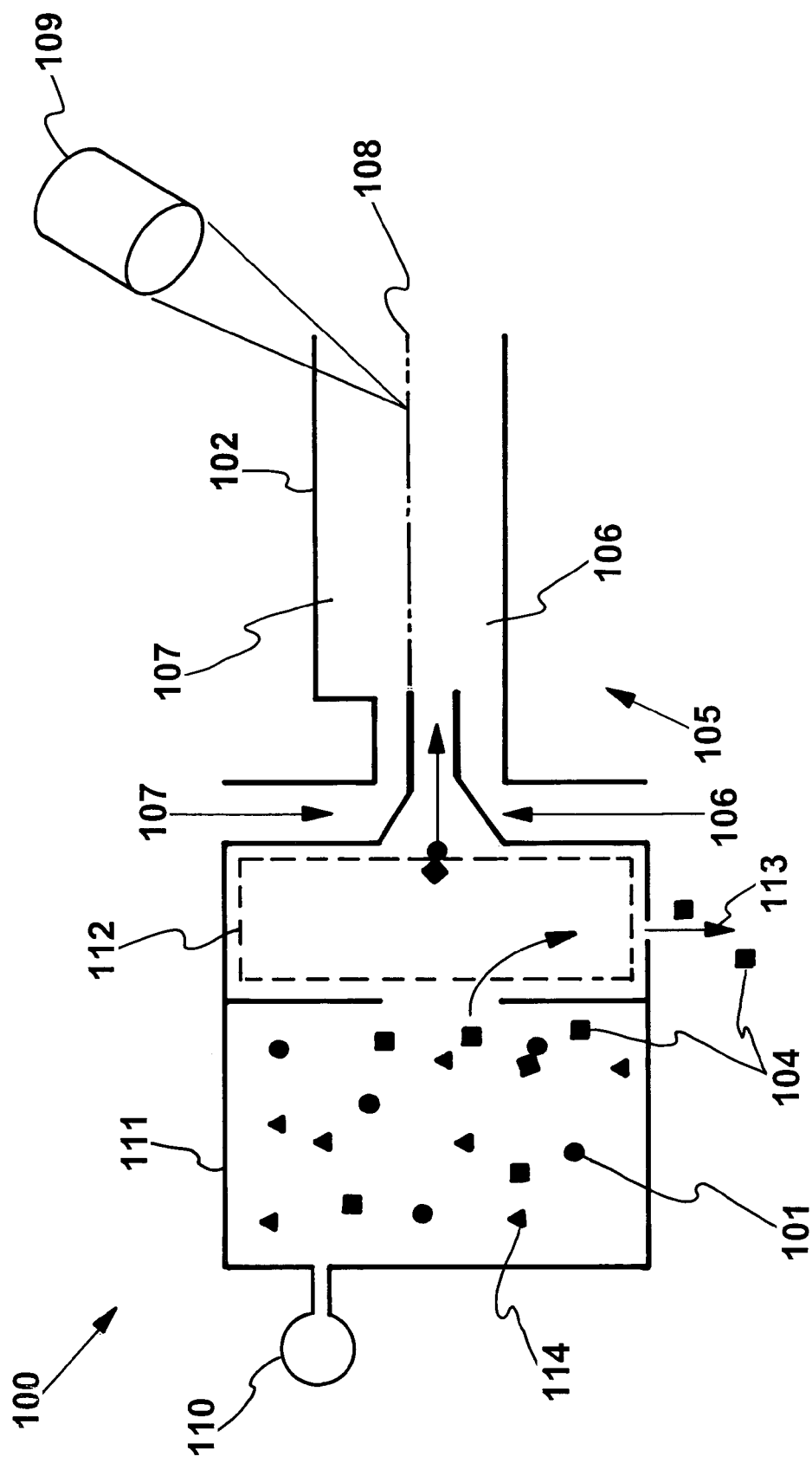
FIG. 1 is an illustration of a system that represents one embodiment of the present invention.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to FIG. 1, one embodiment of a system constructed in accordance with the present invention is illustrated. The system is designated generally by the reference numeral 100. The system 100 provides a micro-flow cytometry system.

Flow cytometry is defined as a technique for identifying and sorting cells and their components (as DNA) by staining with a fluorescent dye and detecting the fluorescence usually by laser beam illumination. The use of flow cytometry for quantitative cell, bead and other particle differentiation has been increasing in the three decades since the basic technology was first introduced. Today's commercially-available systems are relied upon for an array of applications including monitoring in cancer and HIV infection. Furthermore, this invention presents a viable scheme to miniaturize this important technology, which will significantly increase its impact.

Flow cytometry is a tool that is underused given its potential to describe the complex nature of cell populations. Typically, cell processes are characterized by their overall bulk properties by monitoring changes in substrate, product, and byproduct concentrations in the extracellular environment. Flow cytometry has been used to describe the heterogeneity in substrate uptake rates and intracellular protein accumulation, yielding information about cell populations that otherwise remains hidden. In addition, due to the explosion in cell cycle research that has occurred over the past decade, we now know mechanistic details of the regulatory network that play a major role in controlling relevant cellular processes. Moreover, changes in cell cycle distributions observed with flow cytometric data have been shown to be directly correlated to cell growth rates and can be used to predict future trends in growth. Although flow cytometry is an ideal tool that can accurately describe these phenomena, there is an extensive amount of sample preparation required to quantify and analyze changes in cellular properties that occur during a culture process. Thus, it would be desirable to automate the sampling and staining procedures that are necessary for analysis.

The present invention provides a flow cytometry system for detecting a sample. The flow cytometry system includes a mixing cell for mixing a fluid, environmental sample with antibody coated beads for a sandwich assay, the beads are designed to have hydrophilic and hydrophobic hemispheres, the beads are then transported into an amphiphilic separator that is a co-flow of oil and water, the oil-water interface between the oil phase and the waterphase mediates separation and positioning of the detection beads, and an optical detector for detecting the flouresence at the oil-water interface. The amphiphilic platform, the immuno-assay bead, as stated consists of a hydrophilic and hydrophobic hemisphere that when placed in an oil and water combination with an interface between the oil and the water, placing in the amphiphilic platform will preferentially partition to the interface, enabling precise positioning for detection of the sample at the interface. The channel is narrowed in the transverse direction to ensure a "single-file" transport of the amphiphilic detection platform and passed through they micro-flow cytometry. The flow cytometry system also exploits the oil water co-flow to ensure precise control of the oil water interface.

The system 100 illustrated by FIG. 1 shows an oil-water flow cell 102. The sample injection port 110 on the far left of the flow cell 102 connects with a sample preparation system that transfers a pure solution plus target species to a mixing chamber 111. The mixing chamber 111 facilitates interaction between prepared sample, antibody coated beads 101 and free-floating flourescently labeled antibodies 104. After mixing, the unattached antibodies 104 are recycled using a filter 112. The amphiphilic bead 101, target species 114 and fluourescent compound assemblies are injected into the oil-water flow cell 105 and form a 2D layer at the interface 108 that flows past a detector 109. In one embodiment the detector 109 is a laser detector.

The amphiphilic, antibody coated beads 101 are exposed to the sample that contains the target species and flourescently labeled antibodies. Once the beads 101 have captured the target species 114 and the flourescently labeled antibodies 104 attach to the now bound target species 114, the beads 101 are injected into the oil-water flow cell 105. In the oil-water flow cell, the oil phase 106 and the water phase 107 produce the oil-water interface 108 and form a 2D surface of immunoassay beads that are ready for optical detection. Additionally, the fluid and bead densities are tuned to ensure that buoyancy forces also cause the beads to seek the interface. The detection region for detector 109 has now been reduced from 3D to 2D. The amphiphilic layer can then be compressed orthogonal to the flow direction, using well known focusing techniques, e.g., physical or acoustic focusing, prior to optical detection.

Figure 2:
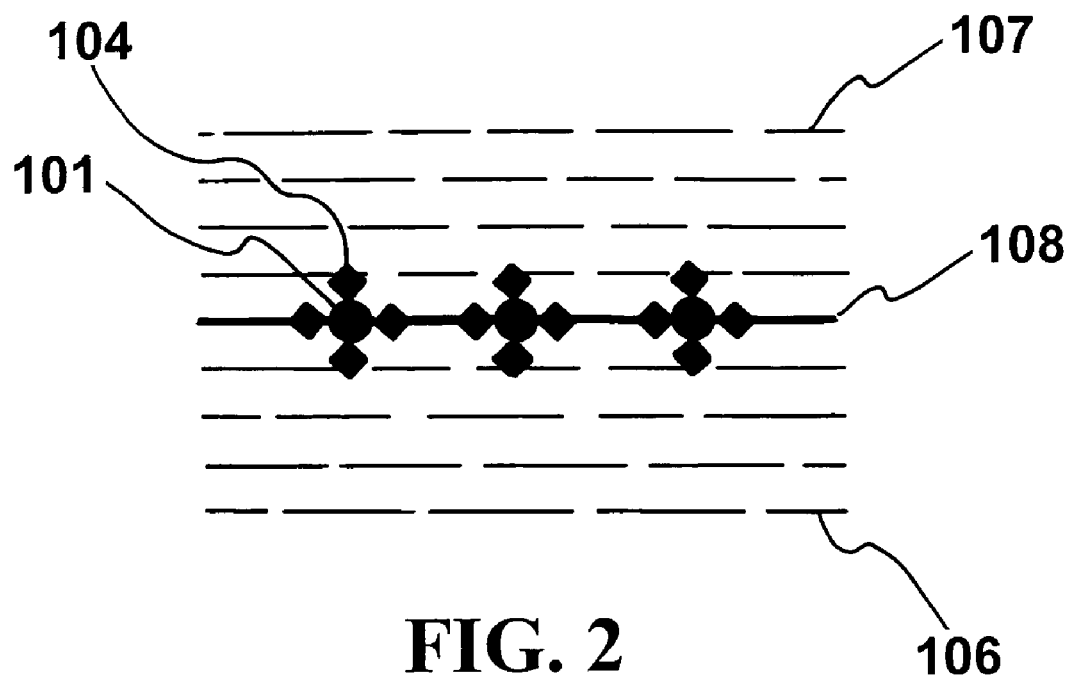
FIG. 2 is an enlarged view of a section of the oil-water flow cell.

Referring now to FIG. 2, an enlarged view of a section of the oil-water flow cell 105 is shown. The amphiphilic beads 101, target species and flourescently labeled antibodies 104 flow into the oil-water flow cell 105 and form a 2D layer at the interface 108. The oil-water interface 108 is established between the oil phase 106 and the water phase 107. The fluid and bead densities are tuned to ensure that buoyancy forces also cause the beads to seek the interface 108. The amphiphilic layer can then be compressed orthogonal to the flow direction, using well known focusing techniques, e.g., acoustic focusing, prior to optical detection. The detection region for detector 109 has now been reduced from 3D to 2D. The oil-water interface 108 provides the 2D surface of immunoassay beads that are ready for optical detection.

Figure 3:
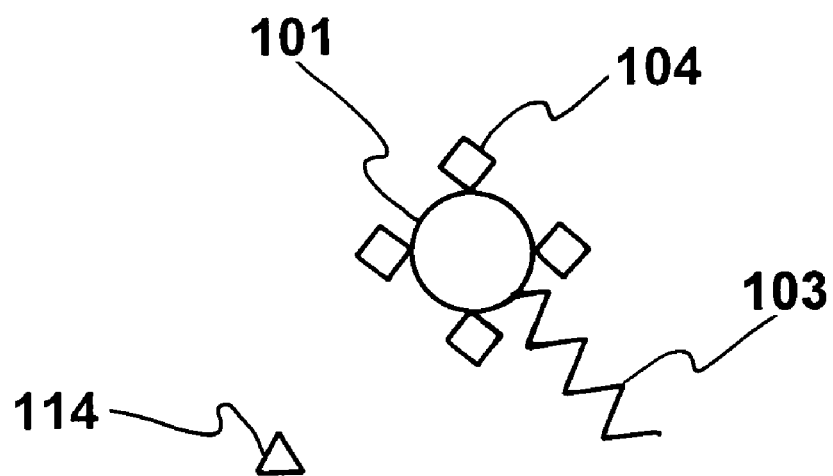
FIG. 3 is an illustration of some of the components of the system illustrated in FIGS. 1 and 2.

Referring now to FIG. 3, some of the components of the system 100 are illustrated. The amphiphilic beads 101, flourescently labeled antibodies 104, and target species are shown. The amphiphilic, antibodycoated beads 101 are exposed to the sample that contains the target species and flourescently labeled antibodies. The mixing in the mixing chamber 11 provides an interaction between the prepared sample, the antibody coated beads 101 and the free-floating flourescently labeled antibodies 104. Once the beads 101 have captured the target species 114 and the flourescently labeled antibodies 104 attach to the now bound target species 114, the beads 101 are injected into the oil-water flow cell 105. A functionalized bead 101 is shown with attached antibodies 104 and a hydrocarbon, hydrophobic tail group 103, which gives the bead the amphiphilic character. $\rho_1$, $\rho_2$ and $\rho_B$ are the densities of the water, oil and bead respectively.

Referring now to the FIGS. 1, 2, and 3, the system 100 represents one embodiment of the present invention. The system 100 utilizes functionalized, amphiphilic beads 101 and an oil-water flow cell 102. The system 100 provides a microflow cytometer that makes use of two-phase microflows; namely, the flow cell has a co-flow of oil 106 and water 107 to ensure that the functionalized beads 101 will seek the interface 108 between the liquid layers due to both buoyancy and hydrophobic-hydrophilic effects. The system 100 includes a sample injection port 110, a mixing chamber 111, an antibody filter 112, and an oil-water flow cell 102. The oil-water flow cell 102 includes a microchannel 105 with co-flow of oil 106 and water 107 and an interface 108 between the oil 106 and water 107 layers. An antibody filter 112 and an antibody recycle stream 113 are connected between the mixing chamber 111 and the oil-water flow cell 102.

The functionalized beads 101, which serve as the amphiphilic platform, have a hydrophobic tail groups on one hemisphere that will seek the oil phase and the unfunctionalized hemisphere of the bead 101 itself remains hydrophilic and will seek the water phase. The hydrophobic tail 103 is a hydrocarbon tail. The hydrophilic hemisphere of the beads 101 have an antibody coating, which is also hydrophilic, that will ensure specific binding to target species. Sample, functionalized amphiphilic beads 101, and fluorescently labeled, free-floating antibodies 104 are mixed together to maximize binding events. The mixed sample is then injected into a microchannel 105 that has a constant flow of oil 106 and water 107 at volumetric flow rates to ensure that the oil water interface 108 is at the desired height. The flourescently labeled, amphiphilic beads 101 rest in the interface 108 and travel down the microchannel 105 for detection by detector 109.

Sample preparation for species detection is critical especially when the concentration of target species is very low compared to the concentration of the other species present. Current bead based immunoassays are batch systems even those with flow cytometry. For batch systems the beads are captured in a filter forming a 2D surface containing fluorescently labeled beads for detection. The reduction from 3D to 2D simplifies the detection step. The batch approach is limited since it is a batch process and requires a number of handling steps. In flow cytometry, fluorescently labeled beads are passed single file through a fluid channel, and eradiated/excited with a laser to check for the presence of the target species. Flow cytometers tend to be bench scale apparatus and therefore not always suitable for use in the field. Ideally, the immunoassay would: be a continuous flow microdevice; reduce the sample domain from 3D to 2D, have precise sample height control and sample transport velocities to ensure detection.

This system 100 provides a microflow cytometer that makes use of two-phase microflows; namely, the flow cell has a co-flow of oil and water to ensure that the functionalized beads will seek the interface between the liquid layers due to both buoyancy and hydrophobic-hydrophilic effects. The amphiphilic beads will seek the oil water interface affording precise positioning for detection. Furthermore the beads will have an antibody coating that will ensure specific binding to target species. Sample, functionalized amphiphilic beads, and fluorescently labeled, free-floating antibodies are mixed together to maximize binding events. The mixed sample is then injected into a microchannel that has a constant flow of oil and water at volumetric flow rates to ensure that the oil water interface is at the desired height. The flourescently labeled amphiphilic beads rest in the interface and travel down the microchannel for detection.

Referring now to FIG. 4, another embodiment of a system constructed in accordance with the present invention is illustrated. The system is designated generally by the reference numeral 400. The system 400 provides a flow system for quantitative cell, bead and other particle differentiation.

The beads 401 flow through an oil-water flow cell 105 and form a 2D layer interface 402. The oil-water interface 102 is established between the water phase 403 and the oil phase 405. The fluid and bead densities are tuned to ensure that buoyancy forces also cause the beads to seek the interface 108. The amphiphilic layer can then be compressed orthogonal to the flow direction, using well known focusing techniques, e.g., physical or acoustic focusing, prior to optical detection. The detection region has now been reduced from 3D to 2D. The oil-water interface 402 provides the 2D surface of immunoassay beads that are ready for optical detection.

Referring now to FIGS. 5 and 6, some of the components of the system 400 are illustrated. Immunoassay beads 401 are coated using a static oil-water interface with amphiphilic surfactants. The amphiphilic surfactants include a surfactant head group 405 and hydrophobic tail group 406. The surfactant head group 405 reacts and attaches to the immunoassay beads 401, coating the lower hemisphere. Once attached, the remaining surface of the beads is coated with specific antibodies resulting in an amphiphilic immunoassay bead that can be multiplexed for several targets.

The beads 401, are injected into the oil-water flow cell. Buoyancy forces of the surfactant head group 405 and hydrophobic tail group 406 cause the beads 401 to seek the interface 402 between the water phase 403 and the oil phase 405. The amphiphilic layer can then be compressed transverse to the flow direction, using well known focusing techniques, e.g., physical or acoustic focusing, prior to optical detection. The detection region has now been reduced from 3D to 2D. The oil-water interface 402 provides the 2D surface of immunoassay beads that are ready for optical detection.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A flow cytometry apparatus for detecting a target species in a sample, comprising:
   a mixing chamber that receives the sample containing a target species, and a hydrophobic unit, said hydrophobic unit comprising a bead with a hydrophobic tail,
   a flow cell connected to said mixing chamber,
   a filter positioned between the mixing chamber and the flow cell,
   an oil component in said flow cell,
   a water component in said flow cell,
   an oil-water interface between said oil component and said water component,
   a detector that detects the target species at said oil-water interface, and wherein the hydrophobic unit operatively connected to the target species that causes said hydrophobic unit and the target species to be at said oil-water interface.

2. The flow cytometry apparatus of claim 1 wherein said hydrophobic unit includes a surfactant head.

3. The flow cytometry apparatus of claim 1 wherein specific antibodies are connected to said bead and the target species.

4. The flow cytometry apparatus of claim 1 wherein flourescently labeled antibodies are connected to said bead and the target species.

5. The flow cytometry apparatus of claim 1 wherein said detector is a laser detector.

6. The flow cytometry apparatus of claim 1 including a sample injection port connected to said mixing chamber.

7. A flow cytometry apparatus for detecting a target species in a sample, comprising:
   a mixing chamber means for receiving the sample containing a target species, and a hydrophobic unit, said hydrophobic unit comprising a bead with a hydrophobictial,
   flow cell means for detecting the sample, said flow cell means connected to said mixing chamber, a filter positioned between the mixing chamber means and the flow cell means, an oil phase in said flow cell means, a water phase in said flow cell means, an oil-water interface between said oil phase and said waterphase, detector means for detecting the target species at said oil-water interface, and wherein the hydrophobic unit means connected to the target species that causes said hydrophobic unit means and the target species to be at said oil-water interface.

8. The flow cytometry apparatus of claim 7 wherein said hydrophobic unit means includes a surfactant head.

9. The flow cytometry apparatus of claim 7 wherein specific antibodies operatively connected to said beads and the target species.

10. The flow cytometry apparatus of claim 7 wherein flourescently labeled antibodies are connected to said bead and the target species.

11. The flow cytometry apparatus of claim 7 wherein said detector means is a laser detector.

12. The flow cytometry apparatus of claim 7 including a sample injection port connected to said mixing chamber.

* * * * *